United States Patent [19]
Halpern

[11] 4,098,577
[45] * Jul. 4, 1978

[54] METHOD AND INDICATOR FOR DETECTING THE LOSS OF INTEGRITY OF A PACKAGE

[75] Inventor: Donald F. Halpern, New Providence, N.J.

[73] Assignee: Bio-Medical Sciences Inc., Fairfield, N.J.

[*] Notice: The portion of the term of this patent subsequent to Aug. 12, 1992, has been disclaimed.

[21] Appl. No.: 580,574

[22] Filed: May 27, 1975

Related U.S. Application Data

[63] Continuation-in-part of Ser. No. 418,486, Nov. 23, 1973, Pat. No. 3,899,295.

[51] Int. Cl.² .................... B65D 73/00; G01N 21/06; G01N 31/22
[52] U.S. Cl. .............................. 23/232 R; 23/254 R; 23/253 TP; 23/230 L; 206/364; 206/459; 206/484
[58] Field of Search .......... 23/253 TP, 232 R, 254 R, 23/230 L; 206/459; 116/114 AM

[56] References Cited

U.S. PATENT DOCUMENTS

| | | | |
|---|---|---|---|
| 1,103,985 | 7/1914 | Murray et al. | 23/253 TP |
| 2,567,445 | 9/1951 | Parker | 23/253 TP X |
| 2,787,238 | 4/1957 | Luce | 23/253 TP |
| 2,995,425 | 8/1961 | Fuhrmann | 23/253 R |
| 3,011,874 | 12/1961 | Deutsch | 23/253 TP |
| 3,093,242 | 6/1963 | Huyck et al. | 206/364 X |
| 3,221,428 | 12/1965 | Fischler et al. | 23/253 TP X |
| 3,899,295 | 8/1975 | Halpern | 23/253 TP |

*Primary Examiner*—Robert M. Reese
*Attorney, Agent, or Firm*—Anthony Lagani, Jr.

[57] ABSTRACT

A system for indicating the integrity of a normally sealed package utilizes a sensor containing a pH sensitive dye which displays a first color in equilibrium with normal atmospheric conditions and a second color when in equilibrium with an artificial atmosphere comprising an acidic gaseous material. When the air normally in the package is displaced by the artificial atmosphere, the pH sensitive dye assumes its second color. Loss of integrity of the sealed package results in loss of the acidic gaseous material. As a consequence, the pH sensitive dye reverts to its first color, thereby signaling the loss of package integrity.

25 Claims, 3 Drawing Figures

METHOD AND INDICATOR FOR DETECTING THE LOSS OF INTEGRITY OF A PACKAGE

CROSS REFERENCE TO RELATED APPLICATIONS

This application is a continuation in-part of U.S. application Ser. No. 418,486 filed Nov. 23, 1973, now U.S. Pat. No. 3,899,295.

BACKGROUND OF INVENTION

Numerous articles and materials are packaged in the course of manufacture under special conditions which maintain or prolong their original quality. Surgical devices, for example, are packaged under aseptic conditions or sterilized after packaging as with heat or radiation. Materials subject to oxidation can be packaged under an inert atmosphere such as nitrogen. It is, of course, desirable that such packages retain their integrity in passing from manufacturer to consumer or user. In addition, it is often desirable to insure that products have not been tampered with or adulterated. Thus pharmaceuticals, perfumes, alcoholic beverages and the like may have unique properties associated with well known trademarks, and it is imperative from the manufacturer's point of view to insure that the packaged product has not been opened and the contents diluted or replaced when the consumer purchases the goods. Various guarantees are often dependent on installation by a skilled serviceman, as with sophisticated electronic components, and it is important to provide a means to ascertain whether the component to be installed is in the same condition as when it left the factory.

Various methods of determining package integrity have been devised; see, for example, U.S. Pat. No. 3,221,428 incorporated herein by reference. The device disclosed and claimed therein relies on reagents which react with aim to destroy or discolor an indicator card.

A related indicator device is taught in U.S. Pat. No. 3,093,242. This device uses an ink with an indicator dye sensitive to ethylene oxide to indicate the sterilization of a package by detecting the presence of ethylene oxide in the package. However, no method of indicating whether package integrity is lost after sterilization has been accomplished.

SUMMARY OF THE INVENTION

It has surprisingly been found that the integrity of a package can be monitored by filling the package with an artificial atmosphere comprising an acidic gaseous material. Loss of integrity of the package results in loss acidic gaseous material. The sensor indicates the loss of the artificial atmosphere.

The sensor comprises a pH sensitive dye e.g. thymol blue. The preferred acidic gas is $CO_2$.

DETAILED DESCRIPTION

Figure 1:
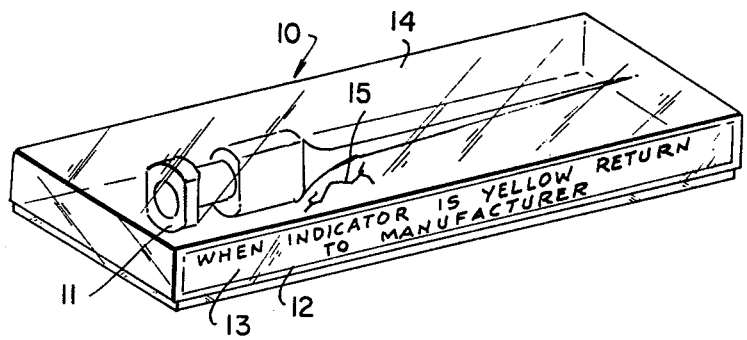
FIG. 1 represents a packaged article with a printed label sensor.

This invention relates to a method detecting the loss of integrity of a sealed package. In particular it relates to a method for detecting such loss of integrity by incorporating into the package at the time of sealing an acidic gaseous material.

The package integrity indicating system comprises (1) an acidic gaseous material, (2) a sensor, and (3) the package enclosure or sealed wrapper. Additionally, a buffering system may be utilized to expand the range selection of dyes used in the sensor.

The sensor is disposed so as to be in communication with the interior of the package but visible from the outside of the package. The sensor can be merely slipped into a transparent package or printed on to the inside surface of the packaging material. Alternatively, the sensor can be structurally integral with the package. For example, where opaque packaging material is used, e.g., aluminum foil, the sensor may be affixed to the foil in a manner so as to be visible from the outside of the package but in communication with the atmosphere within the package. In such a case, the sensor itself may be physically located on the outside of the package or within the package. In either event, the manner of affixing the sensor to the package must be such to maintain package integrity, e.g., pressure sensitive type or heat sealing to the foil by use of a cover strip of transparent film. For example, a package sealed in aluminum foil will have a window opening in the foil. A sensor strip enclosed in a transparent film envelope is heat sealed over the window. The side of the envelope exposed to the interior of the package is slit or otherwise perforated to allow the sensor to be in communication with the atmosphere within the package.

The sensor includes a pH sensitive dye which displays a first color when in equilibrium with normal atmospheric conditions and a second color when exposed to an atmosphere comprising an acidic gaseous material. Loss of integrity of the sealed package results in loss of the acidic gaseous material. As a consequence, the pH sensitive dye reverts to its first color. One of the first "colors" can include a colorless state as will be apparent hereafter.

Illustrative examples of pH sensitive dyes are phenolphthalein, xylenol blue, Nile blue A, m-cresol purple, bromocresol green, o-cresol red, bromophenol red, methyl red, bromothymol blue and phenol red, as well as the alkali and alkaline earth metal salts of such indicators.

The pH sensitive dye can be incorporated in the sensor in any number of ways. It can be simply absorbed on a carrier such as a small dot or strip of paper. Alternatively, it can be printed or stamped in the form of an indicia on a strip of the carrier by incorporating the pH sensitive dye into an ink.

The carrier may be colorless or colored the same or different color as one of the two or more colors of the pH sensitive dye. For example, if the dye changes from blue to yellow, the carrier can be dyed or stained with the same blue tint so that the blue indicia becomes invisible when the dye is in the blue form and visible when the dye is in the yellow form. The sensor can be simple printing on the inside of transparent packaging material utilizing a suitable printing formulation. Such printing can also be a simple dot or similar area with the explanation being printed on the reverse (outside) surface of the film. It will, of course, be desirable to protect any packaged foods from contact with printed sensor.

The second component of the system is an artificial atmosphere which contains a small amount of an acidic gaseous material. This atmosphere is introduced into a package in an amount at least sufficient to maintain the dye of the sensor in its second color. It is to be appreciated that the atmosphere is necessarily "artificial" only in the sense that the acidic gaseous material is present at the indicated level, although it additionally can be artificial for other reasons. For example, the acidic gaseous material can be simply mixed with air or an inert gas to form the artificial atmosphere. Alternatively, the acidic gaseous material can be the only component of the artificial atmosphere. The term "inert gas" means a gaseous material which is not itself an acidic gaseous material or a basic gaseous material.

The term "acidic gaseous materials" as used in the specification and claims means gaseous materials which, when in equilibrium with moisture ($H_2O$) exhibit an acid pH in solution. The term "basic gaseous material" as used in the specification means a gas which when in equilibrium with water results in a solution having a pH greater than 7.0. Illustrative examples of acidic gaseous materials include carbon dioxide, the halogens such as chlorine and bromine as well as the oxy-halides, e.g., $Cl_2O$.

An essential part of the package integrity detection system is the overwrap of the package to be monitored. This overwrap can be the only packaging material. The overwrap must itself be substantially impervious with respect to the acidic gaseous material and be capable of being sealed with sufficient integrity to prevent leakage of the acidic gaseous material. The term "substantially impervious" as used in the specification and claims means having a sufficiently low permeability with respect to the acidic gaseous material so as to prevent loss of the acidic gaseous material below the level sufficient to maintain the sensor at its first color during the shelf life of the packaged article.

Illustrative examples of suitable overwrap materials are polymeric materials, especially films and metal foil.

Illustrative examples of polymeric films are polyvinylidene chloride, teflon, and polytriflurochloroethylene. Composite films may also be used. Illustrative of such composite is saranex, a sandwich of polyvinylidene chloride between two layers of polyethylene.

Illustrative examples of metal foil are aluminum foil and foils of aluminum bronze.

Referring now to FIG. 1, there is shown a package 10 within which article 11 is sealed. Within the package is a sensor 12 which has legend 13 printed thereon. The material with which the legend is printed contains a dye (thymol blue) which is blue when in equilibrium with normal atmospheric conditions but yellow when in equilibrium with an acidic gaseous environment. The package is sealed containing an atmosphere including carbon dioxide in sufficient concentration to hold the dye of the sensor in its yellow form.

Figure 2:
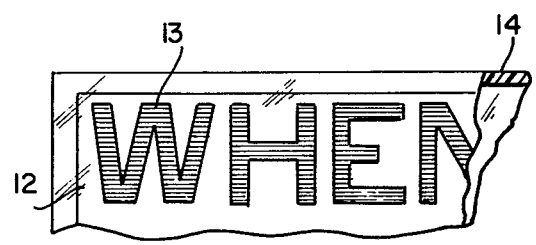
FIG. 2 represents a sealed package with a printed sensor.
Figure 3:
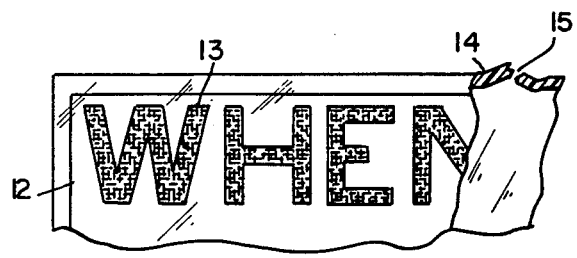
FIG. 3 represents the package of FIG. 2 after loss of integrity.

If the integrity of the package is lost, as for example by a rupture of the package wall 14 in FIG. 2 as shown at 15 in FIG. 3, carbon dioxide escapes and the partial pressure of the carbon dioxide drops. As the pH within the sensor increases as a result of loss of acidic gaseous material, the dye of the sensor reverts to its first color. Accordingly, a user is immediately apprised of the fact that package integrity has been lost, even though the rupture may be too small for, or hidden from, visual inspection.

The nature of the indicia obviously is a matter of choice depending upon whether the dye goes from colored to colorless, colorless to colored, or from color to another color.

A further embodiment involves the incorporation in the sensor of a buffering compound which shifts the operable range of gaseous pressures required to change the indicator into its second color sensor. This permits a somewhat broader selection of dyes and indicator sensitivity. With carbon dioxide as the acidic gas, for example, a dye such as thymol blue can be mixed with sodium hydroxide.

In the presence of carbon dioxide, the dye will assume its yellow color whereas under the influence of normal atmospheric conditions the basicity of the buffer will convert the dye to the dye's blue color. (Other buffers, such as alkali metal phosphates and salts of amines with strong acids can be employed in a similar fashion.)

The term "buffering compound" when used with respect to a carbon dioxide system, means hydroxides and carbonates of alkali metals and alkaline earth metals and bicarbonates of alkali metals as well as tetraorgano ammonium hydroxides.

Illustrative examples of buffering compounds are $Na_2CO_3$, $NaHCO_3$, $NaOH$, $LiOH$, trimethyl benzyl ammonium hydroxide and tetramethyl ammonium hydroxide.

The dye can be applied by formulating a simple ink, as for example by compounding with an alcohol such as butanol, including polyols such as glycerol, polyethylene glycol and the like. The vehicle is not critical and can be compounded according to the practice of the printing art. Where the active form of the dye is sufficiently soluble it can be formulated directly. The dye may also be in the form of a salt or as the free acid or free base, whichever is most convenient for solubility purposes, and then converted to the desired pH form by back titration with acid or base, whichever is appropriate, after printing.

The minimum level of the acidic gaseous material depends upon the particular dye. Some dyes such as ethyl bis (2,4-dinitrophenyl) acetate have poor sensitivities and can only be used where the partial pressure of the acidic gaseous material is high, i.e., about 80% of the total atmosphere. Other dyes such as thymol blue or thymolphthalein are more sensitive and can be used at lower partial pressures, e.g., 7 to 10% of the total or lower. When carbon dioxide is the acidic gaseous material, it often contributes to product stability, as with certain foods.

Foods which may be advantageously packaged in a carbon dioxide atmosphere are cheeses, processed meats, fresh meats, baked goods, nut meats, candies, etc.

The following examples will serve to further typify the nature of the invention without being a limitation on the scope thereof, the invention being defined solely by the appended claims.

EXAMPLE 1

To 20 parts by volume of glycerol is added one part of thymol blue. Eight parts by volume of 10N potassium hydroxide solution are then added to completely dissolve the dye. This ink is then employed to print an indicia, as for example the legend "WHEN THIS INDICATOR IS BLUE RETURN TO MANUFACTURER" on a slip of paper. The printed paper is inserted in a plastic package so as to be visible from the outside. Sufficient carbon dioxide to convert the dye to its second color is then introduced and the package is sealed. So long as package integrity is maintained, the legend remains yellow. If package integrity is lost, the legend reverts to its blue color.

EXAMPLE 2

The ink prepared in Example 1 is utilized to print, in reverse letters, a suitable indicia on a heat sealable plastic film. Objects are then sealed in the film in an artificial atmosphere containing a small amount of carbon dioxide with the printing on the inside of the film.

EXAMPLE 3

A printing material is prepared from 1 part by weight of cresol red, 20 parts by volume of glycerol and up to 5 parts by volume of 10N aqueous potassium hydroxide. This ink is employed in the same fashion described in Example 1.

EXAMPLE 4

A dispersion of 31.8 parts by weight of phenolphthalein in 250 parts by volume of methanol is mixed with a solution of 11.22 parts by weight of potassium hydroxide in 100 parts by volume of methanol. The mixture is then treated with petroleum ether to precipitate out the potassium salt of phenolphthalein which is briefly held under vacuum to remove most of the solvent. One part by weight of this material is then combined with 10 parts by weight of glycerine. This formulation is utilized to print the legend "OPENDED" or Whatman No. 1 filter paper and covered with a heat shrinkable plastic film. The film is then used to envelop the bottom circumference of the cap of the bottle and the neck of the bottle. This is done under atmosphere containing carbon dioxide in an amount sufficient to render the printing colorless. So long as the integrity of the seal is maintained, the printing is invisible. If the seal is broken, the carbon dioxide escapes and the printing becomes visible as the dye turns red to pink.

EXAMPLE 5

One part by weight of Nile blue A is dissolved in 10 parts by volume of glycerol. This material is titrated with a saturated solution of sodium carbonate until a magenta color is obtained. A disc of Whatman filter paper is immersed in the solution and then adhered to the interior of a transparent plastic container. Carbon dioxide is introduced into the container until the disc turns blue and the container is sealed. The sensor will remain blue until the package is opened, after which it will quickly revert to the magenta color. Suitable explanatory information can be printed on or affixed to the outside of the package, ideally in registry with the indicator.

EXAMPLE 6

One part by weight of thymol blue is mixed with 5 parts by weight of polyethylene glycol 200. This mixture is titrated with 10 N aqueous potassium hydroxide until the pH value of the solution reaches 14. Five parts of distilled water is then added and 1 cm disc of Whatman #1 filter paper is impregnated with this solution. The then impregnated disc is inserted into a heat sealable pouch or coextruded polyvinylidene chloride and polyethylene of 5 mil thickness. Carbon dioxide is then introduced into the pouch until the disc turns orange-yellow color and the pouch is sealed ultrasonically. This sensor will turn to blue color if the carbon dioxide partial pressure drops substantially below the initial value. Suitable warning indicia may be printed in association with the sensor.

EXAMPLE 7

Circular dots of ¼ inch diameter are punched from a neutralized cellulostic paper and positioned in the center of a 1 inch wide strip of polyethylene film at intervals of about 1 inch. The polyethylene backing is then sealed to the dots with a counter pressure heat seal and the strip fed through a dip bath of a solution of $2 \times 10^{-3}$M thymol blue and $8 \times 10^{-2}$M sodium hydroxide in an aqueous medium containing 15% glycerol. The strip is next passed through an air knife squeegee to remove liquid from the hydrophobic backing sheet and excess liquid from the sealed dots. The strip is next perforated transversely to its longitudinal axis in order to provide tear lines mid-way between each dot and the strip is then rolled in a sealed polystyrene dispensing cartridge. The individual indicators are removed from the roll, separated and sealed to the inside of a transparent package of Milprint film (a laminate of Mylar M-24, Surlyn and polyethylene) with the paper dot against the inside surface of the package.

The indicator is heat sealed to the package only on a portion of its outside perimeter so as to permit gas passage between the package and backing sheet. A food product, such as sausage or luncheon meat, is then inserted and an atmosphere containing about 15% carbon dioxide is introduced and the package sealed. The sealed plastic package is in turn packaged in an outer cardboard box having a precut aperture to reveal the paper dot of the indicator and a suitable legend, such as "SEALED WHEN YELLOW" printed about the aperture.

The pH of a solution in equilibrium with normal atmospheric conditions can vary depending upon a variety of factors, especially levels of oxides of carbon, nitrogen and sulphur in the air. The pH at which the color change of the indicator dye occurs will, however, generally be within the range of about 6.7 to about 9.2 where an acidic gas is used with a buffering system.

What is claimed is:

1. A visual package integrity indicator system comprising a normally sealed package, a sensor in communication with the interior of said package but visual from the exterior of said package, said sensor including a pH sensitive dye system which displays a first color when in equilibrium with normal air and a second color when in equilibrium with an acidic gaseous material, and an artificial atmosphere within said package, said artifical atmosphere comprising an acidic gaseous material, said gaseous material being sufficient to maintain said dye system in its second color when said package is sealed, said dye system being reversibly responsive to the presence or absence of said artificial atmosphere whereby said dye reverts to its first color when the artificial atmosphere is lost as a result of package seal being broken.

2. A package integrity indicator system according to claim 1 wherein said acidic gaseous material is carbon dioxide.

3. A package integrity indicator system according to claim 1 wherein said package is transparent and said sensor is indicia printed on the inside surface of said package.

4. A package integrity indicator system according to claim 1 wherein said dye system includes a pH sensitive dye and a buffering compound.

5. The package integrity system of claim 1 wherein the artificial atmosphere comprises $CO_2$ enriched air, the $CO_2$ concentration being at least sufficient to cause the pH sensitive dye to assume its second color.

6. The package integrity indicator system of claim 1 wherein the pH sensitive dye is thymol blue, bromocresol green, bromophenol red, or Nile blue A.

7. The package integrity indicator according to claim 1 wherein the artificial atmosphere comprises $CO_2$ in an amount at least sufficient to cause the pH sensitive dye to assume its second color and an inert gas.

8. The system of claim 7 wherein the inert gas is nitrogen.

9. The package integrity indicator system of claim 1 wherein the sealed package is sealed in an overwrap of a material selected from the group consisting of polymeric films and metal foils.

10. The system of claim 9 wherein the polymeric film is polyvinylidiene chloride, teflon, polytrifluorochlorethylene, or a laminate of polyvinylidiene chloride between two layers of polyethylene.

11. The system of claim 9 wherein the foil is aluminum foil.

12. A package integrity indicator system according to claim 1 wherein said acidic gaseous material is carbon dioxide and said pH sensitive dye undergoes a color change in the pH range of 6.7 to 9.2.

13. A package integrity indicator system according to claim 12 wherein said package is transparent and said sensor is indicia printed on the inside surface of said package.

14. A package integrity indicator system according to claim 12 wherein said package is transparent and said sensor is inserted in said package.

15. A package integrity indicator system according to claim 12 wherein said dye system includes a pH sensitive dye and a buffering compound.

16. A package integrity indicator system according to claim 12 wherein said atmosphere comprises nitrogen and carbon dioxide.

17. A package integrity indicator system according to claim 1 wherein the sensor comprises a pH sensitive dye in combination with a polyol and a buffering system.

18. A package integrity indicator system according to claim 17 wherein the acidic gaseous material is $CO_2$.

19. A package integrity indicator system according to claim 17 wherein the polyol is glycerol.

20. A package integrity indicator system according to claim 19 wherein the buffering compound is NaOH, $Na_2CO_3$ or $NaHCO_3$ and the acidic gaseous material is $CO_2$.

21. The package integrity indicator system of claim 20 wherein the pH sensitive dye is thymol blue.

22. A process for detecting the loss of integrity of a sealed package which comprises:
(a) filling the package prior to sealing with an artificial atmosphere comprising an acidic gaseous material;
(b) incorporating in the package a sensor comprising a pH sensitive dye, said dye displaying a first color when in equilibrium with normal air and a second color when in equilibrium with said artificial atmosphere; and
(c) sealing the package;
said acidic gaseous material being sufficient to maintain the dye in its second color whereby damage to the package results in loss of artificial atmosphere, resulting in the reversion of the dye to its first color.

23. The process of claim 22 wherein the sealed package is sealed in an overwrap of a material selected from the group consisting of polymeric films and metal foils.

24. The process of claim 23 wherein the polymer film is polyvinylidene chloride, teflon, polytrifluorochloroethylene, or a laminate of polyvinylidene chloride between two layers of polyethylene.

25. The process of claim 24 wherein the foil is aluminum foil.

* * * * *